(12) United States Patent
Zhu et al.

(10) Patent No.: US 12,338,271 B2
(45) Date of Patent: Jun. 24, 2025

(54) FUSION PROTEIN INCLUDING GIP AND FGF21 AND COMPOSITIONS THEREOF

(71) Applicant: JIANGNAN UNIVERSITY, Wuxi (CN)

(72) Inventors: Shenglong Zhu, Wuxi (CN); Yongquan Chen, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 0 days.

(21) Appl. No.: 18/313,282

(22) Filed: May 5, 2023

(65) Prior Publication Data

US 2024/0002461 A1  Jan. 4, 2024

Related U.S. Application Data

(63) Continuation of application No. PCT/CN2022/073492, filed on Jan. 24, 2022.

(30) Foreign Application Priority Data

Jun. 10, 2021  (CN) .......................... 202110650331.X

(51) Int. Cl.
| | | |
|---|---|---|
| *A61K 38/18* | (2006.01) | |
| *A61P 1/16* | (2006.01) | |
| *C07K 14/50* | (2006.01) | |
| *C07K 14/645* | (2006.01) | |
| *A61K 38/00* | (2006.01) | |

(52) U.S. Cl.
CPC .............. *C07K 14/645* (2013.01); *A61P 1/16* (2018.01); *C07K 14/50* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 9,475,850 B2 | 10/2016 | Chugh | |
| 2017/0096462 A1 | 4/2017 | Mohammadi et al. | |

FOREIGN PATENT DOCUMENTS

| | | |
|---|---|---|
| CN | 101155828 A | 4/2008 |
| CN | 101993496 A | 3/2011 |
| CN | 103945871 A | 7/2014 |
| CN | 105324125 A | 2/2016 |
| CN | 107266579 A | 10/2017 |
| CN | 108350054 A | 7/2018 |
| CN | 110229238 A | 9/2019 |
| CN | 111892650 A | 11/2020 |
| CN | 113265007 A | 8/2021 |

OTHER PUBLICATIONS

Min Chen et al., "Correlation analysis of serum fibroblast growth factor 21 with insulin resistance and islet beta-cell function in patients with type 2 diabetes mellitus" Chinese J Health Lab Tec. Dec. 2016, vol. 26, No. 24, pp. 3566-3568 (Dec. 25, 2016).

*Primary Examiner* — Christine J Saoud
(74) *Attorney, Agent, or Firm* — SZDC Law PC

(57) ABSTRACT

The invention provides a fusion protein for treating metabolic diseases, and a preparation method and use thereof. The fusion protein has a general formula of R1-L-R2 or R2-L-R1, wherein R1 is FGF21 protein, an FGF21 protein analog, or a similar peptide with the biological function of FGF21 protein; R2 is GIP, mutant GIP or a similar peptide with the biological function of GIP; and L is a linker peptide. The fusion protein of the present invention is used as a therapeutic agent or a pharmaceutical composition in the treatment of diseases associated with hyperglycemia and hyperlipidemia, including diabetes, obesity, steatohepatitis or cardiovascular diseases,

3 Claims, 3 Drawing Sheets

Specification includes a Sequence Listing.

FUSION PROTEIN INCLUDING GIP AND FGF21 AND COMPOSITIONS THEREOF

This application is a Continuation Stage Application of PCT/CN2022/073492, filed on Jan. 24, 2022, which claims priority to Chinese Patent Application No. 202110650331.X, filed on Jun. 10, 2021, which is incorporated by reference for all purposes as if fully set forth herein.

A Sequence Listing XML file named "10015_0120.xml" created on Oct. 9, 2024, and having a size of 11,758 bytes, is filed concurrently with the specification. The sequence listing contained in the XML file is part of the specification and is herein incorporated by reference in its entirety.

FIELD OF THE INVENTION

The present invention relates to the technical field of medicine, and particularly to a fusion protein for treating metabolic diseases, and a preparation method and use thereof.

DESCRIPTION OF THE RELATED ART

Fibroblast growth factor (FGF) 21 is a new member of the FGF family, and the FGF21 gene is mainly expressed in the liver and fat. FGF21 can promote the glucose consumption by HepG2 cells and 3T3-L1 adipocytes in vitro, and has the function of lowering blood glucose and triglycerides in animals, without causing hypoglycemia, tumor development and other side effects (Kharitonenkov A, et al. FGF21 as a novel metabolic regulator. J Clin Invest 2005; 115:1627-35. Kharitonenkov A, et al. The metabolic state of diabeticmonkeys is regulated by fibroblast growth factor-21. Endocrinology 2007; 148:774-81). FGF21, due to the characteristics of safe, effective, and insulin-independent regulation of blood glucose levels in organisms, is expected to be a new treatment for type II diabetes. However, numerous clinical trials have found that the FGF21 analogs do not significantly ameliorate the blood glucose level in patients with diabetes. This may be attributed to the activity and in-vivo stability of the FGF21 analogs designed by these companies. Therefore, more effective modifications of wild-type FGF21 have gradually become a research hotspot in recent years.

Gastric inhibitory polypeptide (GIP) or glucose-dependent insulinotropic peptide (GIP) is a hormone produced by K cells in the mucosa of the small intestine, which can inhibit the gastric acid secretion; inhibit the pepsinogen secretion; stimulate the insulin release; inhibit the peristalsis and emptying of a stomach; stimulate the secretion of intestinal fluid; and stimulate the secretion of glucagon.

FGF21 can break down the fat, reduce the body weight, and improve the lipid metabolism, but has no function of lowering blood glucose. Although GIP can promote the insulin secretion, it also stimulates an increase in glucagon. If GIP is mutated, to retain its function of stimulating insulin secretion, the new GIP will be complementary to FGF21 in terms of the biological activity. The two can regulate blood glucose through corresponding receptors on different target cells or different receptors on the same target cells. If their functions can be combined effectively, the blood glucose is controlled, the fat is broken down, and the body weight is reduced. For the treatment of diabetes and obesity, dual function has significant advantages over simple FGF21 analog.

SUMMARY OF THE INVENTION

The present invention aims to provide a fusion protein having the biological activities of both FGF21 and GIP. The fusion protein is used as a therapeutic agent or a pharmaceutical composition in the treatment of diseases associated with hyperglycemia and hyperlipidemia, including diabetes, obesity, steatohepatitis or cardiovascular diseases.

According to the technical solution of the present invention, the fusion protein has a general formula of R1-L-R2 or R2-L-R1, where R1 is FGF21 protein, a FGF21 protein analog or a similar peptide with the biological function of FGF21 protein; R2 is GIP, mutant GIP or a similar peptide with the biological function of GIP; and L is a linker peptide.

Preferably, the FGF21 protein analog has an amino acid sequence that is as shown in SEQ ID NO: 1 or SEQ ID NO: 2, or that is the amino acid sequence of SEQ ID NO: 1 or SEQ ID NO: 2 with one or more amino acid residue substitutions or deletions.

Preferably, the mutant GIP has an amino acid sequence that is as shown in SEQ ID NO: 3 or SEQ ID NO: 4, or that is the amino acid sequence of SEQ ID NO: 3 or SEQ ID NO: 4 with one or more amino acid residue substitutions or deletions. The similar peptide with the biological function of GIP may be a similar peptide having 40% or more homogeneity with SEQ ID Nos: 3-4 and retaining the biological activity of GIP.

Preferably, the linker peptide consists of 0-30 amino acids.

Preferably, the FGF21 protein has an amino acid sequence as shown in SEQ ID NO: 1 or SEQ ID NO: 2, GIP has an amino acid sequence as shown in SEQ ID NO: 3, the linker peptide consists of 0 amino acid, and the FGF21 protein is located at the C terminus of the fusion protein.

Preferably, the linker peptide is selected from the linker peptides of general formulas a-d:
  a: (Gly-Gly-Gly-Gly-Ser) n-(Ser) m, in which n is any integer from 0 to 5, and m is 0 or 1, when n is 1 and m is 1, the sequence thereof is shown in SEQ ID NO: 8;
  b: (Gly-Gly-Gly-Gly-Ser) n'-(Ser-Pro) m', n' is any integer from 0 to 5, and m' is 0 or 1, when n' is 1 and m' is 1, the sequence thereof is shown in SEQ ID NO: 9;
  c: (Pro-Glu-Ala-Pro-Thr-Asp) n'', n'' is any integer from 0 to 5, when n'' is 1, the sequence thereof is shown in SEQ ID NO: 10; and
  d: (Ser-Ser-Ser-Ser-Gly) n'''-(Ser-Pro) m''', n''' is any integer from 0 to 5, and m''' is 0 or 1, when n''' is 1 and m''' is 1, the sequence thereof is shown in SEQ ID NO: 11.

Preferably, the fusion protein further comprises pharmaceutically acceptable modifications for half-life extension, where the modification is selected from the group consisting of a polymer modification, an unstructured peptide chain modification, an elastin-like polypeptide modification, a serum protein modification, a serum protein binding molecule modification, an immunoglobulin modification, a Fc region modification of immunoglobulin and any combination thereof.

A second aspect of the present invention provides a gene encoding any of the fusion proteins described above.

A third aspect of the present invention provides a vector carrying the gene above.

A fourth aspect of the present invention provides a microbial cell comprising the vector above.

A fifth aspect of the present invention provides a method for preparing the fusion protein, which includes the following steps:
  S1: expressing the fusion protein in the microbial cell; and
  S2: isolating and purifying the fusion protein.

A sixth aspect of the present invention provides a pharmaceutical composition comprising the fusion protein for treating metabolic diseases, where the treatment of metabolic diseases comprises one or more of inhibiting the weight gain, lowering the blood lipid and blood glucose, improving the insulin sensitivity, reducing the liver weight and liver triglyceride level, repairing liver damage, inhibiting the expression of inflammatory factors, ameliorating non-alcoholic steatohepatitis, ameliorating atherosclerosis, ameliorating liver damage, ameliorating liver cirrhosis and liver cancer, ameliorating primary biliary cholangitis and ameliorating primary sclerosing cholangitis.

Preferably, the pharmaceutical composition further comprises one or more of a pharmaceutically acceptable carrier, excipient, and diluent.

Preferably, the pharmaceutical composition is administered by oral administration, intraperitoneal injection, subcutaneous injection, intravenous or intramuscular injection.

A sixth aspect of the present invention provides use of the fusion protein and the pharmaceutical composition in the preparation of drugs for treating metabolic diseases, including one or more of diabetes, obesity, hepatitis and hepatitis related diseases.

Preferably, the dose of the fusion protein is 1-100 mg/kg.

Compared with the prior art, the technical solution of the present invention has the following advantages:

(1) Compared with the original FGF21 analog, the novel dual-targeting fusion protein of the present invention has the efficacy of more effectively, stably, and potently treating obesity, overweight, metabolic syndrome, diabetes, hyperglycemia, abnormal blood lipid level, non-alcoholic steatohepatitis (NASH), atherosclerosis, liver damage, liver cirrhosis, liver cancer, primary biliary cholangitis (PBC) and primary sclerosing cholangitis (PSC).

(2) Unlike GIP, the novel dual-targeting fusion protein of the present invention causes no side effects such as gastrointestinal distress and loss of appetite in the treatment process, and has little influence on the normal life activities of the body.

DETAILED DESCRIPTION OF THE PREFERRED EMBODIMENTS

Figure 1:
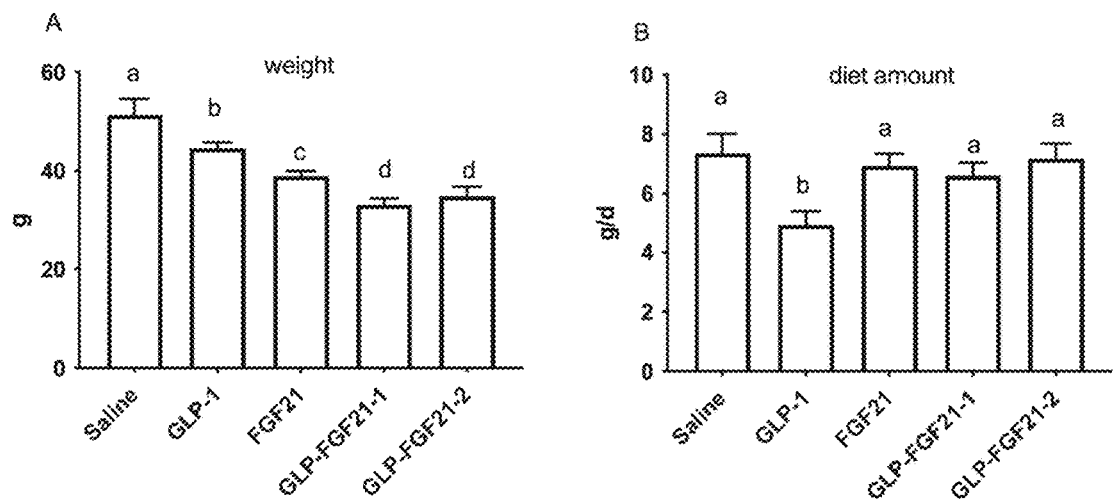
FIG. 1 shows the effects of 4 proteins on the body weight and food intake of db/db mice (A: weight; B: diet amount).

The present invention will be further described below with reference to the accompanying drawings and specific examples, so that those skilled in the art can better understand and implement the present invention; however, the present invention is not limited thereto.

Test animals and feeding: db/db mice purchased from Shanghai SLAC Laboratory Animal Co., Ltd., raised in the Animal Center of Wuxi Medical College, Jiangnan University, with cyclic lighting every 12 hrs, and at 20±2° C.

Other agents are analytical pure and made in China.

Example 1: Construction, Expression and Purification of Recombinant Protein (1) Construction of GIP-FGF21-1 and GIP-FGF21-2 Expression Vectors Based on computer simulations of the substitution and codon preference in E. coli, two novel fusion protein coding genes were designed, where the amino acid sequences of the two fusion proteins were respectively GIP-FGF21-1 (as shown in SEQ ID NO: 5), GIP-FGF21-2 (as shown in SEQ ID NO: 6) shown in the sequence listing. The two genes were sent to Shanghai Generay Biotech Co., Ltd for synthesis, and two restriction sites of NdeI and BamHI were designed at both ends of each gene. The 2 synthetic vectors containing their respective target gene fragments and pET30a (+) were digested by NdeI and BamHI, respectively. After digestion, respective target fragment needed was recovered by extraction. The 4 target fragments were respectively ligated to the prokaryotic expression vector pET30a (+) by T4 DNA ligase. The ligation system was 10 µL, and mixed well, and the ligation was continued at 4° C. overnight. Then the ligated product was respectively transformed into E. coli DH5a. The positive clone was picked up, enzymatically digested, and identified. Two recombinant plasmids pET30a-GIP-FGF21-1 and pET30a-GIP-FGF21-2 were constructed.

(2) Protein Expression and Purification

The recombinant plasmids pET30a-GIP-FGF21-1 and pET30a-GIP-FGF21-2 of correct sequences was transformed into the expression strain Rosseta (DE3) competent cells. The transformed single colonies were inoculated into 20 mL of LB medium containing Kan (50 µg/mL) respectively, and cultured at 37° C. for 8 hrs. The cell culture was inoculated into another 20 mL of LB medium containing Kan (50 µg/mL) at a volume ratio of 1:100, and cultured at 37° C. When A600 was around 0.35, IPTG was added at a final concentration of 0.25 mmol/L for induction at a temperature of 30° C. 5 hrs later, the cells were harvested, and re-suspended in Lysis buffer (20 mmol/L Tris, 150 mmol/L NaCl, pH8.0). The cell suspension was homogenized, and then centrifuged. The supernatant and pellet were analyzed by 12 wt % SDS-PAGE electrophoresis. The results show that the expression of GIP-FGF21-1 and GIP-FGF21-2 protein in Escherichia coli is significantly increased. The target proteins largely exist in the form of inclusion bodies.

A large number of induced cells were collected, to which lysozyme (1 mg/mL) was added. After standing on ice for 30 min, the cells were ultrasonically homogenized (working for 1s, with an interval of 1s, 4 min/cycle, a total of 3 cycles). After the cells were thoroughly homogenized, the cell homogenate was treated with QuixStand pre-treatment system (750 kD ultrafiltration hollow fiber column). The inclusion body was enriched, and the liquid at the pass-through end of the membrane was discarded. When the total volume was about 60 mL, 100 mL of a washbuffer (20 mmol/L Tris, 2 mol/L Urea, 150 mmol/L NaCl, pH8.0) was added to wash the inclusion body. When the volume of the solution was 50 mL, 100 mL of the washbuffer was added. The test was repeated four times. After washing, when the volume of the solution was 50 mL, the pass-through end was closed. The washed inclusion body was added with 150 mL of a denaturing solution (20 mmol/L Tris, 10 mol/L Urea, 150 mmol/L NaCl, pH 8.0), and cyclically denatured for 2 hrs. The pass-through end was opened, and the liquid at the pass-through end of the membrane was collected, which is the denaturated mFGF21 solution. The denaturated mFGF21 was concentrated by a 5 KD hollow fiber column to a volume of 80 mL and then renatured. A container filled with the renaturing buffer (20 mmol/L Tris, 50 mmol/L NaCl, pH8.0) was connected to a reservoir of a hollow fiber column by a rubber tube. The reservoir was sealed, and the liquid flowed out through the pass-through end. Because of the negative pressure in the reservoir, the renaturing buffer was added dropwise to the denatured protein solution at a certain rate for slow and uniform renaturation. When the volume of the renaturing buffer added was 6 times of the denaturated protein solution, the renaturation was completed. After centrifugation at 8000 rpm/min and 4° C. for 20 min, the supernatant was collected. The renaturated supernatant was completely bound to Capto Q column (packed in a XK16/20 hollow column, column height 10 cm, flow rate 300 cm/h) equilibrated with 5 column volumes of IEX buffer A (20 mmol/L Tris, 10 mmol/L NaCl, pH 8.0) of AKTA purifier 100 system, and washed with 3-4 column volumes of IEX buffer A. When the UV curve reaches a stable baseline, the column was eluted with mixed IEX buffer A and IEX buffer B (20 mmol/L Tris, 1 mol/L NaCl, pH 8.0). 15 wt % and 100 wt % IEX buffer B were used to elute the impurity protein off, and 18.5 wt %-19 wt % IEX buffer B was used to elute the target protein off. Each elution peak was collected, and analyzed by 15 wt % SDS PAGE electrophoresis. The results show that the purity of the purified protein is 95% or more.

Example 2: Effect of Recombinant Protein on Body Weight, Food Intake, Blood Lipid, and DM Related Indexes Following the method in Example 1, FGF21 (as shown in SEQ ID NO: 7), GIP-1 (as shown in SEQ ID NO: 3), GIP-FGF21-1, GIP-FGF21-2 were produced.

50 SPF grade male db/db mice aged 8 weeks were pre-raised for 1 week and then weighed. On the following day, the animals were fasted for 6 hrs, with free access to water. The fasting blood glucose of the mice was determined by sampling blood from the tail vein. The mice with abnormal weight were excluded, and 30 model mice with blood glucose and body weight relatively close to the mean value were screened. They were randomly divided into a Saline group, a FGF21 group, a GIP-1 group, a GIP-FGF21-1 group, a GIP-FGF21-2 group, each having 6 animals. The animals in the test group were given the corresponding test agent once a day at around 8:30 am, by intraperitoneal injection, at a dose of 2 mg/kg, and the animals in the Saline group were injected with the same volume of saline, for consecutive 8 weeks. During the test, the mice were allowed to free access to food and water, and the food intake and body weight of the mice were monitored. After 8 weeks of administration, the mice in each test group were sacrificed (fasting overnight). Eyeball blood was taken to measure the blood glucose. triglycerides (TG), and total cholesterol (TC) levels in mice. The test data were analyzed statistically.

The test data are shown in FIG. 1. The results show that compared to the saline control group, FGF21, GIP-1 and 2 new proteins GIP-FGF21-1 and GIP-FGF21-2 all can significantly reduce the body weight of mice. However, the GIP-1 protein after injection significantly reduces the food intake of mice, and suppresses their appetite. Compared to GIP-1, the 2 new proteins GIP-FGF21-1 and GIP-FGF21-2 can more potently and significantly inhibit the body weight after administration, without affecting the food intake of the mice.

Figure 2:
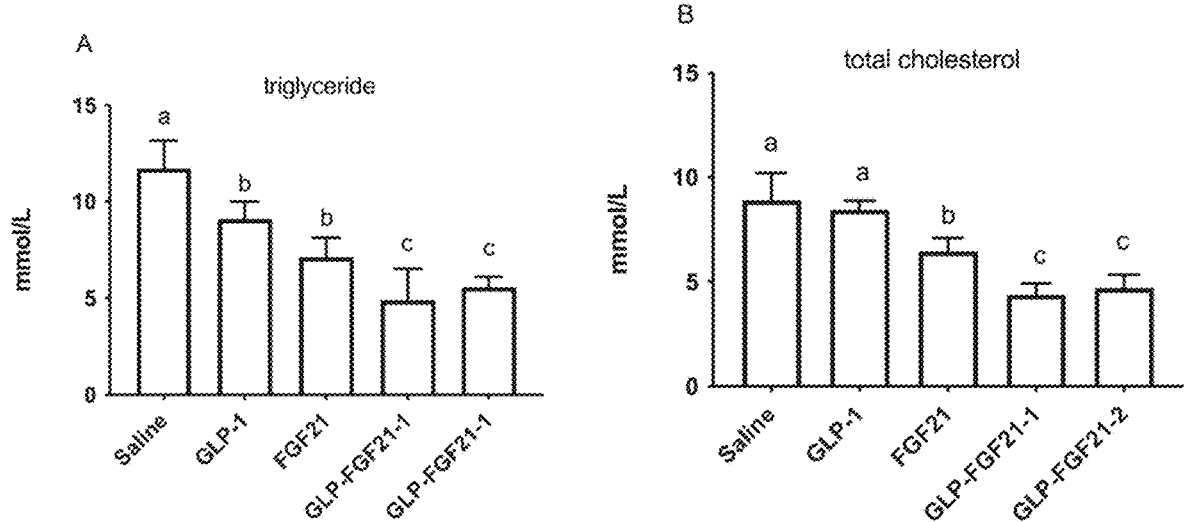
FIG. 2 shows the effects of 4 proteins on the blood lipid of db/db mice (A: triglyceride; B: total cholesterol).

After 8 weeks of administration, the serum lipid levels in mice in each test group are as shown in FIG. 2. Compared to the saline group, FGF21, GIP-1, GIP-FGF21-1, and GIP-FGF21-2 can significantly lower the TG and TC contents in serum after injection. However, the therapeutic effect of GIP-FGF21-1 and GIP-FGF21-2 is better than that of original GIP-1 and FGF21.

Figure 3:
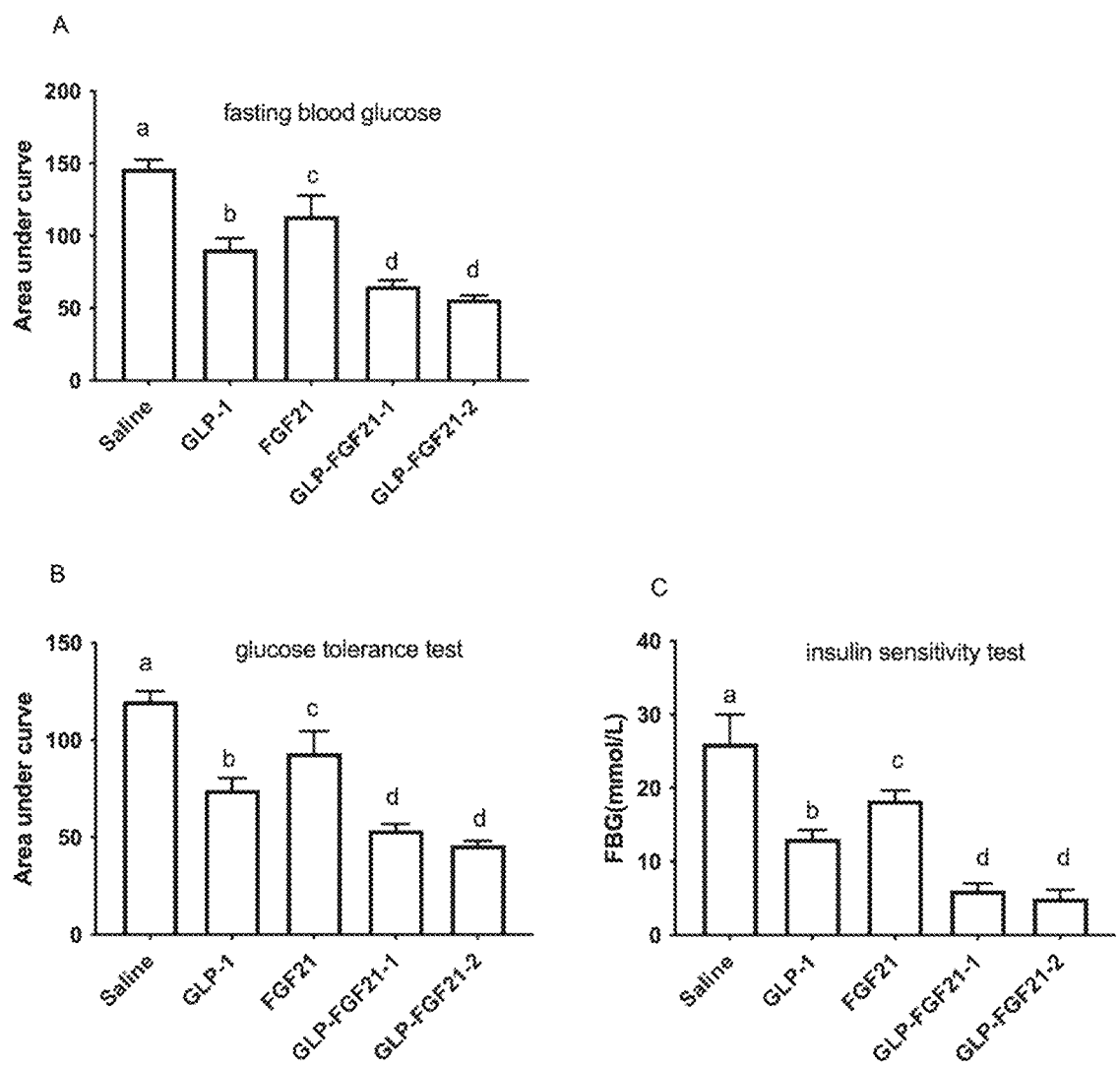
FIG. 3 shows the effects of 4 proteins on DM related indexes in db/db mice (A: fasting flood glucose; B: glucose tolerance test; C: insulin sensitivity test).

After 8 weeks of administration, the fasting blood glucose, insulin sensitivity, and glucose tolerance of mice in all test groups are as shown in FIG. 3. Compared to the saline group, FGF21, GIP-1, GIP-FGF21-1, and GIP-FGF21-2 all can significantly ameliorate the blood glucose level and insulin resistance after injection. However, the therapeutic effect of GIP-FGF21-1 and GIP-FGF21-2 is better than that of original GIP-1 and FGF21.

Example 3: Effects of Recombinant Proteins on Nonalcoholic Steatohepatitis (NASH) Related Indicators Following the method in Example 1, FGF21, GIP-1, GIP-FGF21-1, and GIP-FGF21-2 were produced. 60 SPF grade male C57BL/6 mice aged 8 weeks were pre-raised for 1 week, and then fed on methionine choline deficient MCD diet, for 8 weeks. The mice with abnormal weight were excluded, and 30 model mice with blood glucose and body weight relatively close to the mean value were screened. They were randomly divided into a Saline group, a FGF21 group, a GIP-1 group, a GIP-FGF21-1 group, a GIP-FGF21-2 group, each having 6 animals. The animals in the test group were given the corresponding test agent once a day at around 8:30 am, by intraperitoneal injection, at a dose of 2 mg/kg, and the animals in the Saline group were injected with the same volume of saline, for consecutive 8 weeks. During the test, the mice were allowed to free access to food and water, and After 8 weeks of administration, the mice in each test group were sacrificed (fasting overnight). Triglyceride (TG), alkaline phosphatase (ALP), and alanine aminotransferase (ALT) levels in the liver of test mice were detected and the tissue sections were stained tested for the inflammatory markers. The test data were analyzed statistically.

Figure 4:
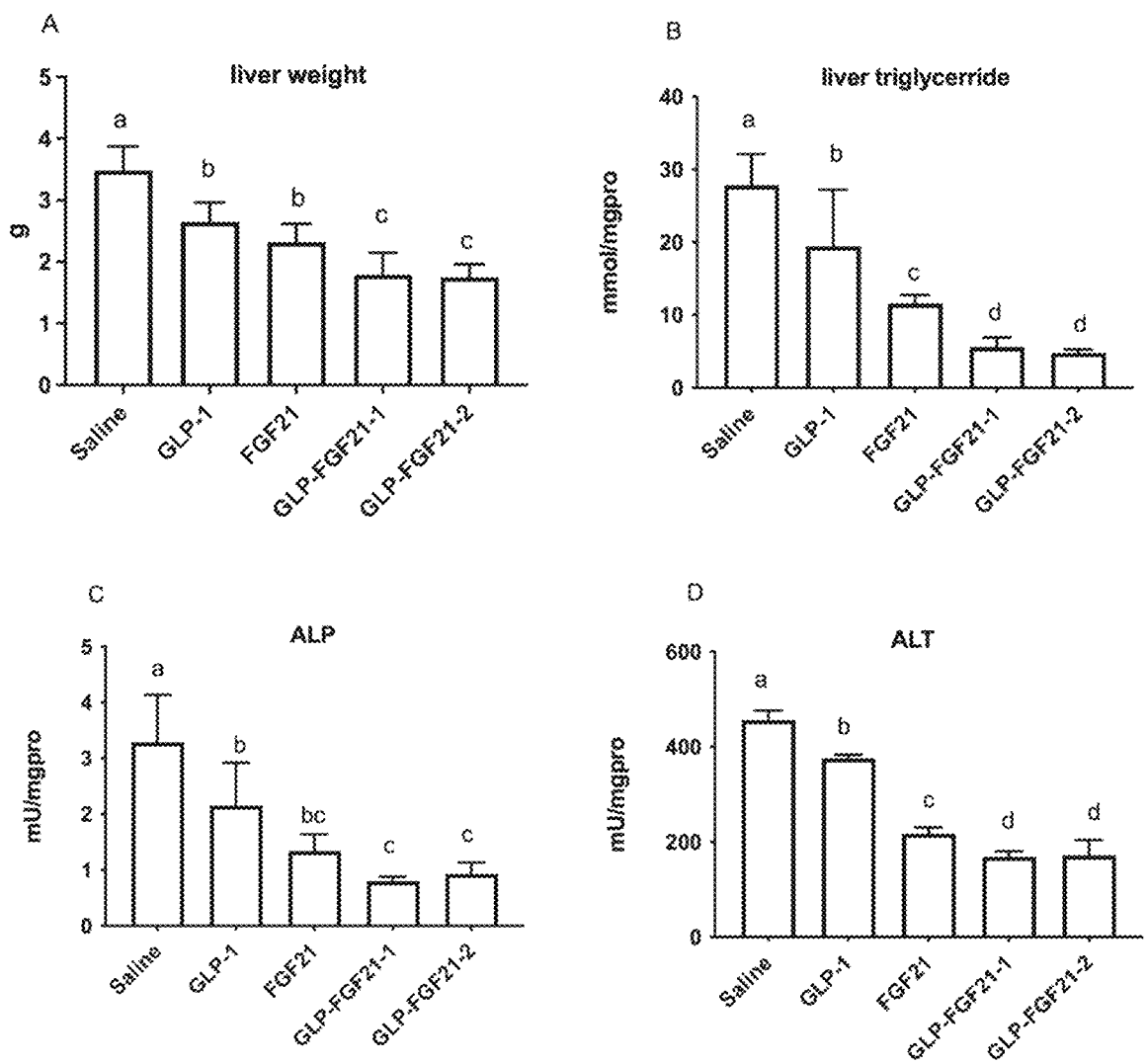
FIG. 4 shows the effects of 4 proteins on steatohepatitis and liver fibrosis in NASH model mice (A: liver weight; B: liver triglyceride; C: alkaline phosphatase (ALP); D: alanine aminotransferase (ALT)).

The test results are shown in FIG. 4. The results in FIGS. 4A and 4B show that compared to the saline control group, FGF21, and GIP-1, and GIP-FGF21-1, and GIP-FGF21-2 all can significantly reduce the liver weight and triglyceride (TG) content in the liver of mice. However, the therapeutic effect of GIP-FGF21-1 and GIP-FGF21-2 is better than that of original GIP-1 and FGF21. The alanine aminotransferase test results in FIGS. 4C and 4D further show that the new proteins GIP-FGF21-1 and GIP-FGF21-2 have obviously better protection against liver damage than original FGF21 and GIP-1. Moreover, the HE staining results directly show that GIP-FGF21-1 and GIP-FGF21-2 can significantly reduce the hepatic vacuoles after injection, and almost no hepatic vacuoles are observed under microscope. Some vacuoles still exist after treatment with FGF21 and GIP-1. The staining result with Sirius red is used to observe the deposition of collagen fibers in the liver, and reflect the liver fibrosis. The results show that the 2 new proteins GIP-FGF21-1 and GIP-FGF21-2 after mutation and modification can both reverse liver fibrosis. In contrast, fibrosis still exists after treatment with FGF21 and GIP-1. The results show that the reversion effect of the modified recombinant protein on hepatic fibrosis is significantly better than that of the original protein. It is found through the indexes above that the fused 2 new proteins GIP-FGF21-1 and GIP-FGF21-2 have significantly better therapeutic efficacy for NASH and liver damage than the original sequences.

Obviously, the above-described embodiments are merely examples provided for clarity of description, and are not intended to limit the implementations of the present invention. Other variations or changes can be made by those skilled in the art based on the above description. The embodiments are not exhaustive herein. Obvious variations or changes derived therefrom also fall within the protection scope of the present invention.

```
                              SEQUENCE LISTING

Sequence total quantity: 11
SEQ ID NO: 1            moltype = AA   length = 209
FEATURE                 Location/Qualifiers
source                  1..209
                        mol_type = protein
                        organism = Synthetic construct
SEQUENCE: 1
DSDETGFEHS GLWVSVLAGL LLGACQAHPI PDSSPLLQFG GQVRQRYLYT DDAQQTEAHL    60
EIREDGTVGG AADQSPESLL QLKALKPGVI QILGVKTSRF LCQRPDGALY GSLHFDPEAC   120
SFRELLLEDG YNVYQSEAHG LPLHLPGNKS PHRDPAPRGP ARFLPLPGLP PALPEPPGIL   180
APQPLETDSM DPFGLVTGLE AVRSPSFEK                                    209

SEQ ID NO: 2            moltype = AA   length = 178
FEATURE                 Location/Qualifiers
source                  1..178
                        mol_type = protein
                        organism = Synthetic construct
SEQUENCE: 2
ADSSPLLQFG GQVRQRYLYT DDAQQTEAHL EIREDGTVGG AADQSPESLL QLKALKPGVI    60
QILGVKTSRF LCQRPDGALY GSLHFDPEAC SFRELLLEDG YNVYQSEAHG LPLHLPGNKS   120
PHRDPAPRGP ARFLPLPGLP PALPEPPGIL APQPPDVGSS DPLSMVGPSQ GRSPSYAS     178

SEQ ID NO: 3            moltype = AA   length = 73
FEATURE                 Location/Qualifiers
source                  1..73
                        mol_type = protein
                        organism = Synthetic construct
SEQUENCE: 3
HAEGTFTSDV SSYLEGQAAK EFIAWLVRGR GYAEGTFISD YSIAMDKIHQ QDFVNWLLAQ    60
KGKKNDWKHN ITQ                                                      73

SEQ ID NO: 4            moltype = AA   length = 81
FEATURE                 Location/Qualifiers
source                  1..81
                        mol_type = protein
                        organism = Synthetic construct
SEQUENCE: 4
HGEGTFTSDL SKQMEEEAVR LFIEWLKNGG PSSGAPPPSY AEGTFISDYS IAMDKIHQQD    60
FVNWLLAQKG KKNDWKHNIT Q                                             81

SEQ ID NO: 5            moltype = AA   length = 282
FEATURE                 Location/Qualifiers
source                  1..282
                        mol_type = protein
                        organism = Synthetic construct
SEQUENCE: 5
HAEGTFTSDV SSYLEGQAAK EFIAWLVRGR GYAEGTFISD YSIAMDKIHQ QDFVNWLLAQ    60
KGKKNDWKHN ITQDSDETGF EHSGLWVSVL AGLLLGACQA HPIPDSSPLL QFGGQVRQRY   120
LYTDDAQQTE AHLEIREDGT VGGAADQSPE SLLQLKALKP GVIQILGVKT SRFLCQRPDG   180
ALYGSLHFDP EACSFRELLL EDGYNVYQSE AHGLPLHLPG NKSPHRDPAP RGPARFLPLP   240
GLPPALPEPP GILAPQPLET DSMDPFGLVT GLEAVRSPSF EK                     282

SEQ ID NO: 6            moltype = AA   length = 251
FEATURE                 Location/Qualifiers
source                  1..251
                        mol_type = protein
                        organism = Synthetic construct
SEQUENCE: 6
HAEGTFTSDV SSYLEGQAAK EFIAWLVRGR GYAEGTFISD YSIAMDKIHQ QDFVNWLLAQ    60
KGKKNDWKHN ITQADSSPLL QFGGQVRQRY LYTDDAQQTE AHLEIREDGT VGGAADQSPE   120
SLLQLKALKP GVIQILGVKT SRFLCQRPDG ALYGSLHFDP EACSFRELLL EDGYNVYQSE   180
AHGLPLHLPG NKSPHRDPAP RGPARFLPLP GLPPALPEPP GILAPQPPDV GSSDPLSMVG   240
PSQGRSPSYA S                                                       251

SEQ ID NO: 7            moltype = AA   length = 178
FEATURE                 Location/Qualifiers
source                  1..178
                        mol_type = protein
                        organism = Synthetic construct
SEQUENCE: 7
ADSSPLLQFG GQVRQRYLYT DDAQRTEAHL EIREDGTVGG AADQSPESLL QLKALKPGVI    60
```

```
QILGVRTPRF LCQRPDGALY GSLHFDPEAC SFRELLLEDG YNVYQSEAHG LPLHLPGNKS    120
PHRDPAPRGP ARFLPLPFLP PALPEPPGIL GPQPPDVGSS DPLSMVGPSQ GRSPSYAS     178

SEQ ID NO: 8            moltype = AA   length = 6
FEATURE                 Location/Qualifiers
source                  1..6
                        mol_type = protein
                        organism = synthetic construct
SEQUENCE: 8
GGGGSS                                                                6

SEQ ID NO: 9            moltype = AA   length = 7
FEATURE                 Location/Qualifiers
source                  1..7
                        mol_type = protein
                        organism = synthetic construct
SEQUENCE: 9
GGGGSSP                                                               7

SEQ ID NO: 10           moltype = AA   length = 6
FEATURE                 Location/Qualifiers
source                  1..6
                        mol_type = protein
                        organism = synthetic construct
SEQUENCE: 10
PEAPTD                                                                6

SEQ ID NO: 11           moltype = AA   length = 7
FEATURE                 Location/Qualifiers
source                  1..7
                        mol_type = protein
                        organism = synthetic construct
SEQUENCE: 11
SSSSGSP                                                               7
```

What is claimed is:

1. A fusion protein, having the amino acid sequence of SEQ ID NO: 5 or SEQ ID NO: 6.

2. The fusion protein according to claim 1, further comprising an extension which increases the half-life of the fusion protein, wherein the extension is selected from the group consisting of a polymer modification, an unstructured peptide chain modification, an elastin-like polypeptide modification, a serum protein modification, a serum protein binding molecule modification, an immunoglobulin modification, an Fc region modification of immunoglobulin and any combination thereof.

3. A composition comprising the fusion protein of claim 1, further comprising one or more of a pharmaceutically acceptable carrier, excipient, or diluent.

* * * * *